United States Patent
Lansonneur et al.

(10) Patent No.: US 12,186,587 B2
(45) Date of Patent: Jan. 7, 2025

(54) HIGH DOSE RATE RADIOTHERAPY TREATMENT PLANNING, SYSTEM AND METHOD

(71) Applicant: Varian Medical Systems, Inc., Palo Alto, CA (US)

(72) Inventors: Pierre Lansonneur, Helsinki (FI); Miriam Krieger, Halle (DE); Michael Folkerts, Carrollton, TX (US); Anthony Magliari, Swansea, IL (US); Daren Sawkey, Ontario (CA)

(73) Assignees: VARIAN MEDICAL SYSTEMS, INC., Palo Alto, CA (US); VARIAN MEDICAL SYSTEMS PARTICLE THERAPY GMBH & CO. KG, Troisdorf (DE); SIEMENS HEALTHINEERS INTERNATIONAL AG, Steinhausen (CH)

( * ) Notice: Subject to any disclaimer, the term of this patent is extended or adjusted under 35 U.S.C. 154(b) by 219 days.

(21) Appl. No.: 17/709,060

(22) Filed: Mar. 30, 2022

(65) Prior Publication Data
US 2023/0310889 A1    Oct. 5, 2023

(51) Int. Cl.
*A61N 5/10* (2006.01)
*G16H 20/40* (2018.01)

(52) U.S. Cl.
CPC ........... *A61N 5/1031* (2013.01); *G16H 20/40* (2018.01); *A61N 5/1038* (2013.01); *A61N 2005/1041* (2013.01); *A61N 2005/1074* (2013.01)

(58) Field of Classification Search
None
See application file for complete search history.

(56) References Cited

U.S. PATENT DOCUMENTS 10,918,886 B2    2/2021    Smith et al.
11,090,508 B2 *  8/2021    Folkerts ............... A61N 5/1031
(Continued)

FOREIGN PATENT DOCUMENTS

EP        4252838 A1 * 10/2013  ............. A61N 5/103
WO  WO-2021259977 A1 * 12/2021  ............. A61N 5/103

OTHER PUBLICATIONS

Lee, Tsair-Fwu et al. "Comparative analysis of SmartArc-based dual arc volumetric-modulated arc radiotherapy (VMAT) versus intensity-modulated radiotherapy (IMRT) for nasopharyngeal carcinoma." J. App. Clinical Medical Physics, vol. 12, No. 4, Fall 2011 (Year: 2011).*

(Continued)

*Primary Examiner* — Thomas R Artman
(74) *Attorney, Agent, or Firm* — Harness, Dickey & Pierce, P.L.C.

(57) ABSTRACT

A method of planning radiation treatment for a patient includes identifying a region of interest of the patient to be treated with radiation and determining a simulated treatment plan for the region of interest based on a statistical analysis between one or more metrics of the identified region of interest and a previously determined predictive dynamics database that includes information regarding the one or more metrics for corresponding regions of interest for a population of patients. The method further includes characterizing the simulated treatment plan with a FLASH Index that compares an ideal FLASH radiation treatment plan to the simulated treatment plan.

19 Claims, 9 Drawing Sheets

(56) References Cited

U.S. PATENT DOCUMENTS

| | | | |
|---|---|---|---|
| 11,103,727 B2* | 8/2021 | Folkers | G06T 7/0012 |
| 11,116,995 B2 | 9/2021 | Khuntia et al. | |
| 11,590,363 B2* | 2/2023 | Petaja | G16H 20/40 |
| 11,786,753 B2* | 10/2023 | Traneus | A61N 5/103 |
| | | | 600/1 |
| 11,992,703 B2* | 5/2024 | Lansonneur | A61N 5/1071 |
| 2017/0165500 A1 | 6/2017 | Flynn et al. | |
| 2020/0282233 A1* | 9/2020 | Folkerts | G16H 20/40 |
| 2020/0282234 A1* | 9/2020 | Folkerts | G06T 7/0012 |
| 2021/0346719 A1* | 11/2021 | Folkerts | A61N 5/1031 |
| 2021/0393981 A1 | 12/2021 | Folkerts et al. | |
| 2021/0393982 A1* | 12/2021 | Lansonneur | A61N 5/103 |
| 2022/0257979 A1* | 8/2022 | Ichihashi | A61N 5/1037 |
| 2022/0409927 A1* | 12/2022 | Petaja | A61N 5/1048 |
| 2023/0063685 A1* | 3/2023 | Ichihashi | A61N 5/103 |
| 2023/0115222 A1* | 4/2023 | Traneus | A61N 5/1043 |
| | | | 600/1 |
| 2023/0191153 A1* | 6/2023 | Petaja | A61N 5/1048 |
| | | | 378/65 |
| 2023/0310889 A1* | 10/2023 | Lansonneur | A61N 5/103 |
| | | | 378/65 |
| 2023/0315272 A1* | 10/2023 | Magliari | G06F 3/04847 |
| | | | 715/771 |
| 2024/0009484 A1* | 1/2024 | Ichihashi | A61N 5/1039 |

OTHER PUBLICATIONS

EPO written opinion on corresponding application published as EP 4252838 A1. (Year: 2024).*
EPO search report on corresponding application published as EP 4252838 A1. (Year: 2024).*
In re Nuijten, 500 F.3d 1346, 1356-57 (Fed. Cir. 2007).
"IEEE Standard Microcomputer System Bus," in ANSI/IEEE Std 796-1983.
"IEEE Standard for a Simple 32-Bit Backplane Bus: NuBus," in ANSI/IEEE Std 1196-1987.
"IEEE Standard for a Chip and Module Interconnect Bus: SBus," in IEEE Std 1496-1993.
"IEEE Standard for a High-Performance Serial Bus," in IEEE Std 1394-2008.

* cited by examiner

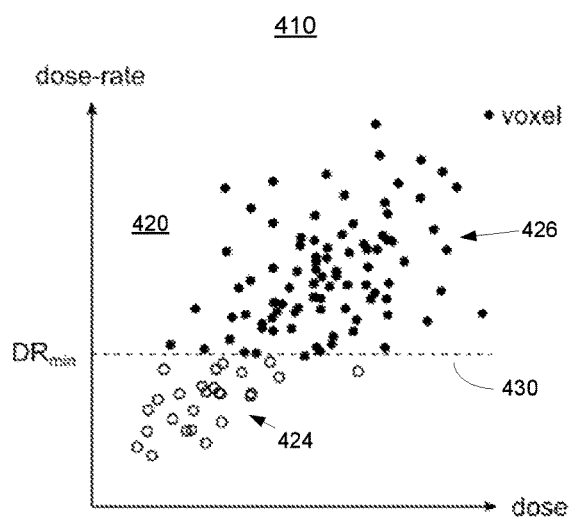
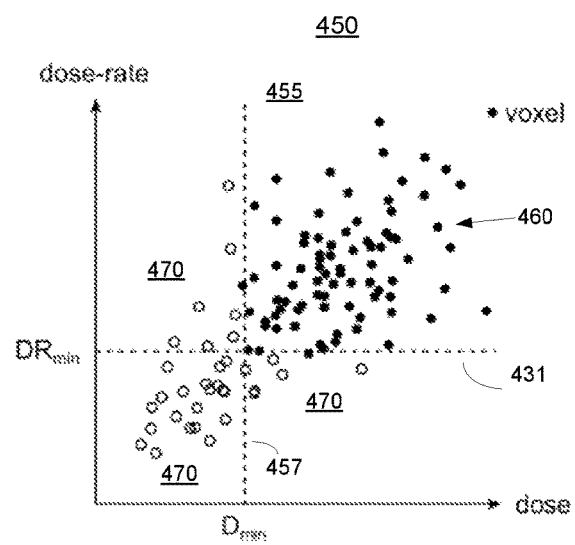
Fig. 4A                                Fig. 4B

850

All Fields

- PTV (852)
- PTV, DR > 40.0 Gy/s (856), FI: 97.7% (858) — (854)
- 860 { Spinal Cord
  Spinal Cord, DR > 40.0 Gy/s, FI: 0.738
- 865 { Heart
  Heart, DR > 40.0 Gy/s, FI: 0.0%
- 870 { Esophagus
  Esophagus, DR > 40.0 Gy/s, FI: 89.1%
- 875 { Tracheobronchial
  Tracheobronchial, DR > 40.0 Gy/s, FI: 0.48
- 880 { Lungs-GTV
  Lungs-GTV, DR > 40.0 Gy/s, FI: 89.0%
- 885 { Great Vessels
  Great Vessels, DR > 40.0 Gy/s, FI: 0.889
- 890 { Patient
  Patient, DR > 40.0 Gy/s, FI: 88.1%

Fig. 8B

HIGH DOSE RATE RADIOTHERAPY TREATMENT PLANNING, SYSTEM AND METHOD

RELATED CASE(S)

The present application is related to U.S. Pat. No. 11,116,995, filed Mar. 6, 2019, U.S. Pat. No. 10,918,886, filed Jun. 10, 2019, and U.S. patent application Ser. No. 17/323,942, filed May 18, 2021. All such Applications and Patents are incorporated herein by reference in their entireties.

FIELD OF INVENTION

Embodiments of the present invention relate to the field of medical devices. More specifically, embodiments of the present invention relate to systems and methods for high dose rate radiotherapy treatment planning.

BACKGROUND

External beam radiation therapy may be used in the treatment of various cancers and non-malignant conditions. Generally, ionizing radiation, including, for example, photons, e.g., X-rays, gamma rays, and charged particles, e.g., protons and electrons, is directed at an area of interest. In many cases, such ionizing radiation is generated by a linear accelerator or a cyclotron.

Before a patient is treated with radiation, a treatment plan specific to that patient is developed. The treatment plan defines various aspects of the therapy using simulations and optimizations that may be based on past experiences. In general, the purpose of the treatment plan is to deliver sufficient radiation to the unhealthy tissue while minimizing exposure of surrounding healthy tissue to the radiation.

The treatment planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find a plan that is best suited to achieving the desired outcome.

FLASH radiotherapy is an emerging radiotherapy regime that appears to reduce radiation-induced toxicities while maintaining a tumor response similar to that of more conventional radiotherapy regimes. This is sometimes known as or referred to as a "FLASH effect." FLASH radiotherapy may be characterized as delivering a high radiation rate, e.g., greater than about 40 Grays (Gy) per second, that allows for a total radiotherapy treatment dose, or large fractions of a total radiation dose, to be delivered in parts of a second, compared to several minutes for conventional radiotherapy. For example, a conventional radiotherapy treatment may include a total dose of 12-25 grays (Gy) delivered at a rate of up to 0.4 Gy/s, requiring minutes of treatment time. In contrast, FLASH radiotherapy may deliver a similar total dose at a rate of 40 Gy/s, requiring a fraction of a second of treatment time.

FLASH radiotherapy introduces important interdependencies that are not captured by conventional radiation treatment planning. Current tools such as dose-volume histograms and dose-rate volume histograms do not capture the interdependence of dose and dose rate. For example, developing a dose rate distribution for a high-quality plan is not trivial from a clinician's perspective because normal tissue might benefit from a low dose rate in certain regions if the dose is minimized in these regions. Also, for example, irradiating a restricted number of spots in a treatment volume may lead to high dose rate delivery but low dose homogeneity at the level of a tumor, while on the other hand, plan quality could be improved by increasing the number of spots at the cost of lowering the dose rate. Further, conventional types of information displays may not provide sufficient information for a clinician to understand many of the characteristics of a FLASH radiotherapy treatment plan.

SUMMARY OF THE INVENTION

Therefore, what is needed are systems and methods for characterizing a FLASH radiotherapy plan. What is additionally needed are systems and methods that compare an ideal FLASH radiation treatment plan to a simulated treatment plan Further, there is a need for systems and methods that compare an ideal FLASH radiation treatment plan to a simulated treatment plan for a plurality of organs at risk. There is a further need for systems and methods for characterizing a FLASH radiotherapy plan that are compatible and complementary with existing systems and methods of planning and/or administering radiotherapy.

In accordance with a method embodiment of the present invention, a method of planning radiation treatment for a patient includes identifying a region of interest of the patient to be treated with radiation and determining a simulated treatment plan for the region of interest based on a statistical analysis between one or more metrics of the identified region of interest and a previously determined predictive dynamics database that includes information regarding the one or more metrics for corresponding regions of interest for a population of patients. The method further includes characterizing the simulated treatment plan with a FLASH Index that compares an ideal FLASH radiation treatment plan to the simulated treatment plan.

In accordance with another method embodiment of the present invention, a method of planning radiation treatment for a patient includes accessing a simulated radiation treatment plan for the patient, determining a FLASH Index for the simulated radiation treatment plan, and displaying the FLASH Index on a graphical user interface on a radiation treatment planning computer system.

In accordance with a further embodiment of the present invention, a non-transitory computer-readable storage medium having computer-executable instructions for causing a computer system to perform a method used for planning radiation treatment, The method includes identifying a region of interest of the patient to be treated with radiation and determining a simulated treatment plan for the region of interest based on a statistical analysis between one or more metrics of the identified region of interest and a previously determined predictive dynamics database that includes information regarding the one or more metrics for corresponding regions of interest for a population of patients. The method further includes characterizing the simulated treatment plan with a FLASH Index that compares an ideal FLASH radiation treatment plan to the simulated treatment plan and displaying the FLASH Index on a graphical user interface of the computer system . . .

BRIEF DESCRIPTION OF THE DRAWINGS

The accompanying drawings, which are incorporated in and form a part of this specification, illustrate embodiments of the invention and, together with the description, serve to explain the principles of the invention. Unless otherwise noted, the drawings may not be drawn to scale.

FIG. 4A illustrates an exemplary plot of dose-rate versus dose for a plurality of voxels of an exemplary treatment plan, in accordance with embodiments of the present invention.

FIG. 4B illustrates a second exemplary plot of dose-rate versus dose for a plurality of voxels of an exemplary treatment plan, in accordance with embodiments of the present invention.

FIG. 8B illustrates an exemplary display image of a Display Legend, in accordance with embodiments of the present invention.

DETAILED DESCRIPTION

Figure 1:
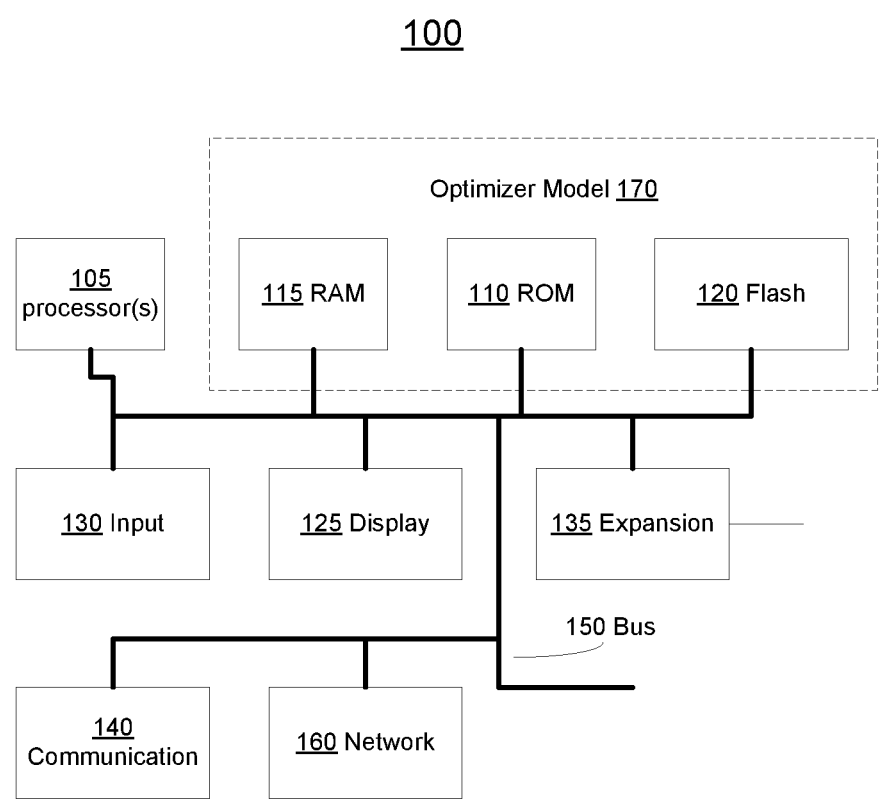
FIG. 1 illustrates a block diagram of an exemplary electronic system, which may be used as a platform to implement and/or as a control system for embodiments of the present invention.

Reference will now be made in detail to various embodiments of the invention, examples of which are illustrated in the accompanying drawings. While the invention will be described in conjunction with these embodiments, it is understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the invention, numerous specific details are set forth in order to provide a thorough understanding of the invention. However, it will be recognized by one of ordinary skill in the art that the invention may be practiced without these specific details. In other instances, well known methods, procedures, components, and circuits have not been described in detail as not to unnecessarily obscure aspects of the invention.

Some portions of the detailed descriptions which follow (e.g., methods 600, 700) are presented in terms of procedures, steps, logic blocks, processing, and other symbolic representations of operations on data bits that may be performed on computer memory. These descriptions and representations are the means used by those skilled in the data processing arts to most effectively convey the substance of their work to others skilled in the art. A procedure, computer executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, data, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "applying" or "controlling" or "generating" or "testing" or "heating" or "bringing" or "capturing" or "storing" or "reading" or "analyzing" or "resolving" or "accepting" or "selecting" or "determining" or "displaying" or "presenting" or "computing" or "sending" or "receiving" or "reducing" or "detecting" or "setting" or "accessing" or "placing" or "forming" or "mounting" or "removing" or "ceasing" or "stopping" or "coating" or "processing" or "performing" or "adjusting" or "creating" or "executing" or "continuing" or "indexing" or "translating" or "calculating" or "measuring" or "gathering" or "running" or the like, refer to the action and processes of, or under the control of, a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The meaning of "non-transitory computer-readable medium" should be construed to exclude only those types of transitory computer-readable media which were found to fall outside the scope of patentable subject matter under 35 U.S.C. § 101 in *In re Nuijten,* 500 F.3d 1346, 1356-57 (Fed. Cir. 2007). The use of this term is to be understood to remove only propagating transitory signals per se from the claim scope and does not relinquish rights to all standard computer-readable media that are not only propagating transitory signals per se.

In the following descriptions, various elements and/or features of embodiments in accordance with the present invention are presented in isolation so as to better illustrate such features and as not to unnecessarily obscure aspects of the invention. It is to be appreciated, however, that such features, e.g., as disclosed with respect to a first drawing, may be combined with other features disclosed in other drawings in a variety of combinations. All such embodiments are anticipated and considered, and may represent embodiments in accordance with the present invention.

High Dose Rate Radiotherapy Treatment Planning, System and Method

FIG. 1 illustrates a block diagram of an exemplary electronic system 100, which may be used as a platform to plan radiation treatments, implement radiation treatments, and/or as a control system for a radiation treatment system. Exemplary radiation systems may be similar to a ProBeam® 360° radiotherapy system or a TrueBeam® radiotherapy system, both of which are commercially available from Varian Medical Systems, Palo Alto, CA. Embodiments in accordance with the present invention are applicable to any type of radiation, including, for example, light ion particles such as protons, alpha particles, or carbon ions, X-rays, and/or electrons, arising from cyclotrons, linear accelerators, and/or other sources.

Electronic system 100 may be a "server" computer system, in some embodiments. Electronic system 100 includes an address/data bus 150 for communicating information, a central processor complex 105 functionally coupled with the bus for processing information and instructions. Bus 150 may comprise, for example, a Peripheral Component Interconnect Express (PCIe) computer expansion bus, industry standard architecture (ISA), extended ISA (EISA), Micro-Channel, Multibus, IEEE 796, IEEE 1196, IEEE 1496, PCI, Computer Automated Measurement and Control (CAMAC), MBus, Runway bus, Compute Express Link (CXL), and the like.

Central processor complex 105 may comprise a single processor or multiple processors, e.g., a multi-core processor, or multiple separate processors, in some embodiments. Central processor complex 105 may comprise various types of well-known processors in any combination, including, for example, digital signal processors (DSP), graphics processors (GPU), complex instruction set (CISC) processors, reduced instruction set (RISC) processors, and/or very long word instruction set (VLIW) processors. In some embodiments, exemplary central processor complex 105 may comprise a finite state machine, for example, realized in one or more field programmable gate array(s) (FPGA), which may operate in conjunction with and/or replace other types of processors to control embodiments in accordance with the present invention.

Electronic system 100 may also include a volatile memory 115 (e.g., random access memory RAM) coupled with the bus 150 for storing information and instructions for the central processor complex 105, and a non-volatile memory 110 (e.g., read only memory ROM) coupled with the bus 150 for storing static information and instructions for the processor complex 105. Electronic system 100 also optionally includes a changeable, non-volatile memory 120 (e.g., NOR flash) for storing information and instructions for the central processor complex 105 which can be updated after the manufacture of system 100. In some embodiments, only one of ROM 110 and/or Flash memory 120 may be present.

Also included in electronic system 100 of FIG. 1 is an optional input device 130. Input device 130 can communicate information and command selections to the central processor complex 105. Input device 130 may be any suitable device for communicating information and/or commands to the electronic system 100. For example, input device 130 may take the form of a keyboard, buttons, a joystick, a track ball, an audio transducer, e.g., a microphone, a touch sensitive digitizer panel, eyeball scanner, and/or the like.

Electronic system 100 may comprise a display unit 125. Display unit 125 may comprise a liquid crystal display (LCD) device, cathode ray tube (CRT), field emission device (FED, also called flat panel CRT), light emitting diode (LED), plasma display device, electro-luminescent display, electronic paper, electronic ink (e-ink) or other display device suitable for creating graphic images and/or alphanumeric characters recognizable to the user. Display unit 125 may have an associated lighting device, in some embodiments.

Electronic system 100 also optionally includes an expansion interface 135 coupled with the bus 150. Expansion interface 135 can implement many well known standard expansion interfaces, including without limitation the Secure Digital Card interface, universal serial bus (USB) interface, Compact Flash, Personal Computer (PC) Card interface, CardBus, Peripheral Component Interconnect (PCI) interface, Peripheral Component Interconnect Express (PCI Express), mini-PCI interface, IEEE 1394, Small Computer System Interface (SCSI), Personal Computer Memory Card International Association (PCMCIA) interface, Industry Standard Architecture (ISA) interface, RS-232 interface, and/or the like. In some embodiments of the present invention, expansion interface 135 may comprise signals substantially compliant with the signals of bus 150.

A wide variety of well-known devices may be attached to electronic system 100 via the bus 150 and/or expansion interface 135. Examples of such devices include without limitation rotating magnetic memory devices, flash memory devices, digital cameras, wireless communication modules, digital audio players, and Global Positioning System (GPS) devices.

System 100 also optionally includes a communication port 140. Communication port 140 may be implemented as part of expansion interface 135. When implemented as a separate interface, communication port 140 may typically be used to exchange information with other devices via communication-oriented data transfer protocols. Examples of communication ports include without limitation RS-232 ports, universal asynchronous receiver transmitters (UARTs), USB ports, infrared light transceivers, ethernet ports, IEEE 1394, and synchronous ports.

System 100 optionally includes a network interface 160, which may implement a wired or wireless network interface. Electronic system 100 may comprise additional software and/or hardware features (not shown) in some embodiments.

Various modules of system 100 may access computer readable media, and the term is known or understood to include removable media, for example, Secure Digital ("SD") cards, CD and/or DVD ROMs, diskettes and the like, as well as non-removable or internal media, for example, hard drives, solid state drives (SSD), RAM, ROM, flash memory, and the like.

In the example of FIG. 1, the memory 115, 110, and/or 120 includes computer-readable instructions, data structures, program modules, and/or the like associated with an "optimizer" model 170. However, the optimizer model 170 may instead reside in any one of the computer storage media used by the system 100, or may be distributed over some combination of the computer storage media, or may be distributed over some combination of networked computers. The functionality of the optimizer model 170 is further described below.

Figure 2:
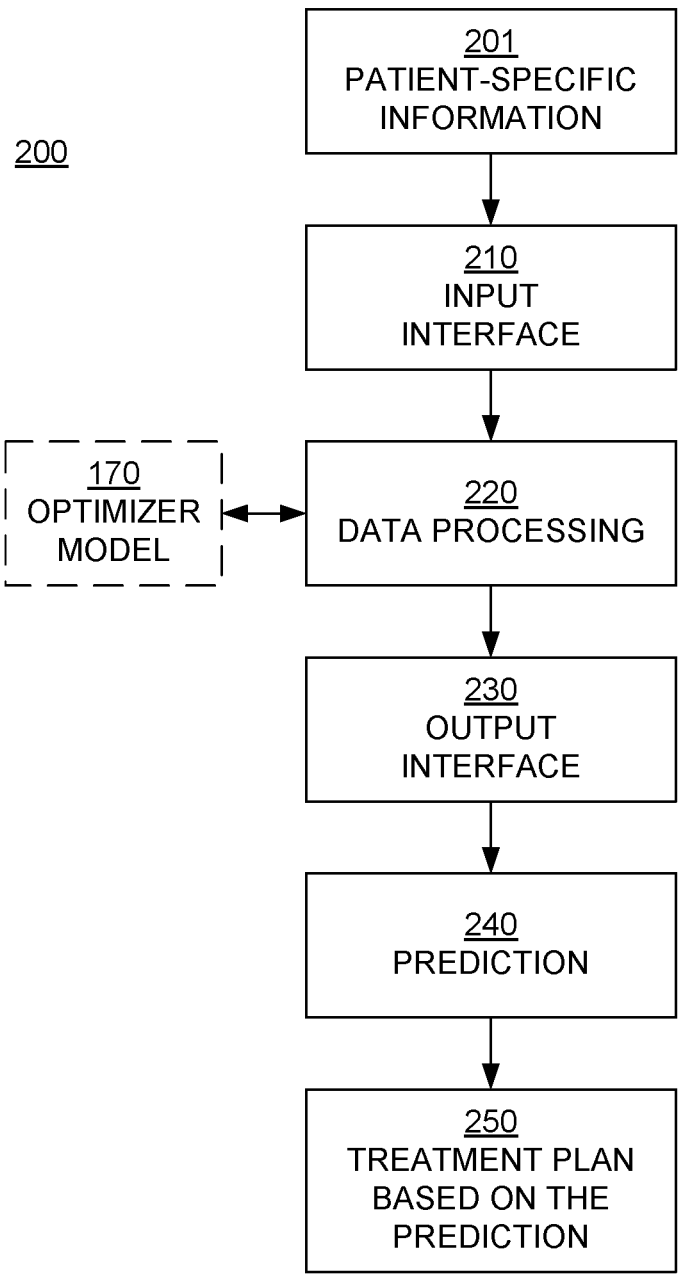
FIG. 2 is a block diagram illustrating an example of an automated radiation therapy treatment planning system, in accordance with embodiments of the present invention.

FIG. 2 is a block diagram illustrating an example of an automated radiation therapy treatment planning system 200, in accordance with embodiments of the present invention. The planning system 200 includes an input interface 210 to receive patient-specific information (data) 201, a data processing component 220 that implements the optimizer model 170 (FIG. 1), and an output interface 230. The planning system 200 in whole or in part may be implemented as a software program, hardware logic, or a combination thereof on and/or using the computer system 100 (FIG. 1).

In the example of FIG. 2, patient-specific information is provided to and processed by the optimizer model 170. In embodiments, the optimizer model 170 yields a prediction result 240, and a treatment plan 250 based on the prediction result can then be generated.

Figure 3:
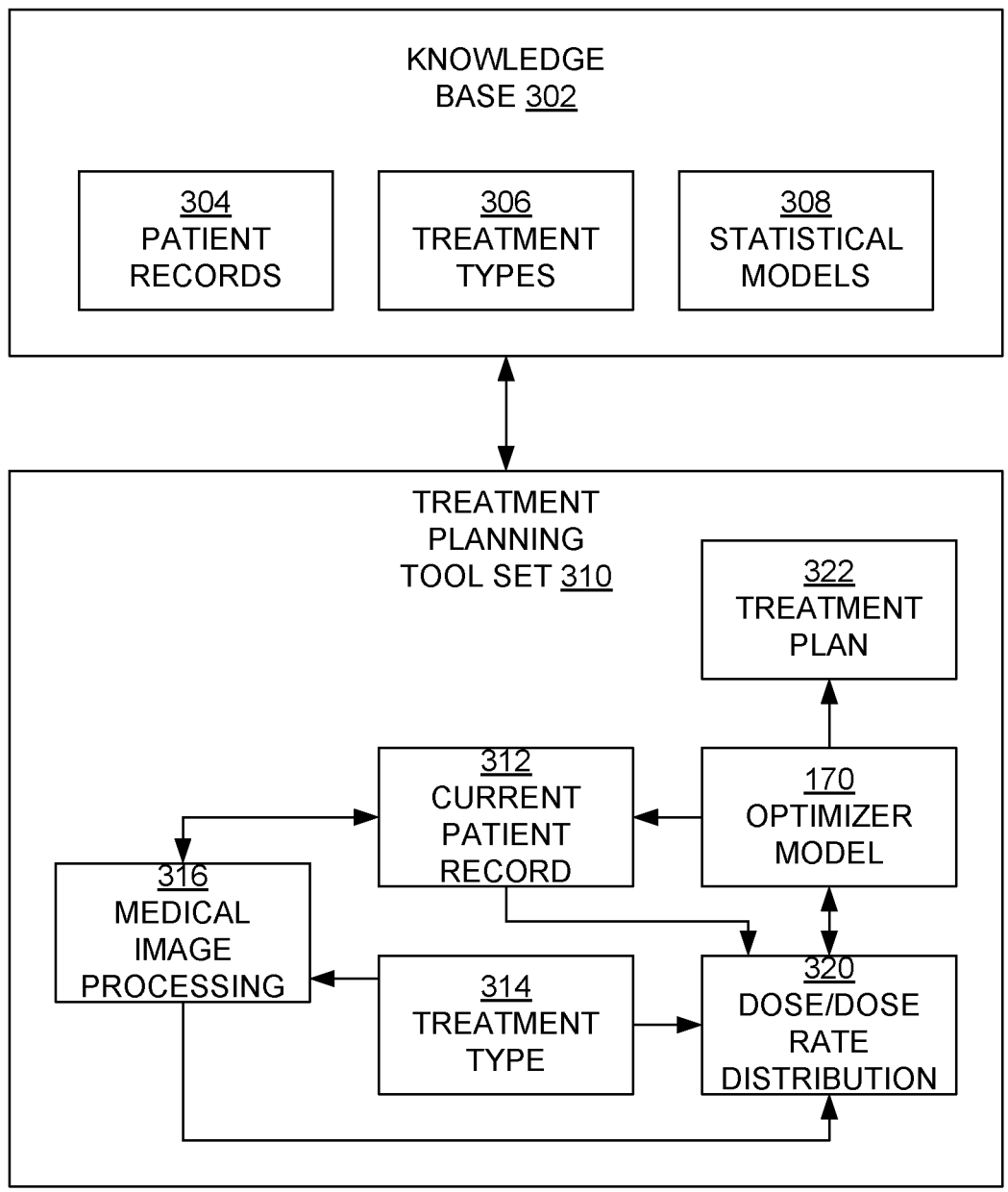
FIG. 3 illustrates an exemplary knowledge-based planning system, in accordance with embodiments of the present invention, in accordance with embodiments of the present invention.

FIG. 3 illustrates an exemplary knowledge-based planning system 300, in accordance with embodiments of the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 170, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, based on past clinical experience, e.g., comprising a previously determined predictive dynamics database that includes information regarding one or more metrics for corresponding regions of interest for a population of patients, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. Patient outcomes, which can include normal tissue complication probability as a function of dose rate and patient-specific treatment-type outcomes (e.g., local recurrent failure, and overall survival as a function of a dose and/or dose rate) can be included in the treatment planning process. The medical image processing module 316 provides automatic contouring and automatic segmentation of two-dimensional cross-sectional slides (e.g., from any imaging modality such as, but not limited to, computed tomography (CT), positron emission tomography-CT, magnetic resonance imaging, and ultrasound) to form a three-dimensional (3D) image using the medical images in the current patient record 312. Dose distribution maps and dose rate distribution maps are calculated by the dose and dose rate distribution module 320, which may utilize the optimizer model 170.

In accordance with embodiments of the present invention, the optimizer model 170 may use a dose prediction model to provide model outputs. Model outputs may include, for example, a 3D dose distribution, fluences, dose rates, and/or associated dose-volume histograms (DVHs) and dose rate-dose-volume histograms (DRDVHs). These model outputs may represent a portion or all of a potential treatment plan. This information may reside in data structures in computer readable memory, e.g., stored within memories 215 and/or 220 (FIG. 2), and may be displayed, e.g., via display 225 (FIG. 2), for review by a clinician.

Due to a variety of factors, it is difficult to develop a treatment plan that meets the criteria to achieve benefits of FLASH radiotherapy, both within a target volume and in adjacent structures, including, for example, organs at risk (OARs). Such difficulties arise, for example, due to technology limitations of a radiotherapy system, e.g., limitations of dose rate, limitations of beam diameter, and/or limitations of beam aim.

Conventional displays of a potential treatment plan are not satisfactory in indicating what portions of such a treatment plan correspond to FLASH radiotherapy. In accordance with embodiments of the present invention, a novel FLASH Index is determined and may be displayed to a clinician as an element in an evaluation of a radiotherapy treatment plan. The novel FLASH Index characterizes a simulated treatment plan with a single quantity, e.g., a percentage, that compares an ideal FLASH radiation treatment plan to the simulated treatment plan. A FLASH Index may also be determined for individual tissues, for example, organs at risk (OARs), in some embodiments. For example, a radiotherapy treatment plan may be characterized with a single FLASH Index and/or with a plurality of FLASH Indexes corresponding to a plurality of tissues, including, for example, organs at risk.

For a given tissue structure, e.g., an organ or portion of an organ, the FLASH Index is maximal (equal to 1) when all of the conditions to observe a FLASH effect are satisfied and minimal (equal to 0) when none of the conditions are satisfied. Such conditions may be expressed as, for example:

Total dose>10 Gy,
Mean dose-rate>40 Gy/s,
Total delivery time<100 ms,

The values given here are examples and can vary with tissue type and other biological conditions or markers. These data can directly be computed per voxel in a treatment planning system (TPS), and the FLASH Index (FI) can be calculated for an arbitrary volume or organ-at-risk (OAR), based on one or more of several factors, including:

minimum dose-rate,
minimum dose,
maximum delivery time.

In some embodiments, calculation of the FLASH Index based on these parameters may use the Heaviside function $H(x)$, as shown below in Relation 1:

$$H(x) = \begin{cases} 0, & \text{if } x < 0 \\ 1, & \text{if } x \geq 0 \end{cases} \quad \text{(Relation 1)}$$

If the only factor considered is the radiotherapy dose rate, a FLASH Index may be expressed as shown in Relation 2, below:

$$FI_{OAR} = \frac{\sum_i H(DR_i - DR_{min})}{N_{voxOAR}}, \quad \text{(Relation 2)}$$

where $DR_i$ is a dose rate for a voxel index $i$, $DR_{min}$ is a minimum dose rate of consideration, and $N_{vox,OAR}$ is the total number of voxels contained in the structure.

If the factors considered are dose rate and minimum voxel dose, a FLASH Index may be expressed as shown in Relation 3, below:

$$\frac{\sum_i H(DR_i - DR_{min}) \cdot H(D_i - D_{min})}{N_{voxOAR}}, \quad \text{(Relation 3)}$$

Where $D_i$ is a dose for a voxel index $i$, and $D_{min}$ is a minimum dose of consideration.

If dose rate, minimum voxel dose, and delivery time are considered as factors, a FLASH Index may be expressed as shown in Relation 4, below:

$$FI_{OAR} = \frac{\sum_i H(DR_i - DR_{min}) \cdot H(D_i - D_{min}) \cdot H(T_{max} - T_i)}{N_{voxOAR}} \quad \text{(Relation 4)}$$

where Ti is a time for a voxel index i, and Tmax is a maximum time of consideration.

The FLASH Index for an organ-at-risk (OAR) may also be determined using functions other than the Heaviside step function H(x) described above. For example, a simple linear weighting of dose could emphasize the assumed FLASH effect in higher dose regions. Even still, at standard (non-FLASH) dose rates, the probability of tissue damage increases with dose, at a rate greater than linear. The probability of a cell surviving a high linear energy transfer (LET) radiation dose D may be written S(D)=exp(−αD), for an empirical value a which may be found in scientific literature. Equivalently the probability of a cell being killed is P(D)=1−exp(−αD). If this expression is used instead of the Heaviside or linear function, the FLASH Index for an OAR may be expressed as shown in Relation 5, below:

$$FI_{OAR} = \frac{\sum_i H(DR_i - DR_{min}) \cdot [1 - \exp(-\alpha D_i)]}{N_{voxOAR}} \quad \text{(Relation 5)}$$

Moreover, the FLASH Index of an OAR may also be weighted, for example, as disclosed with respect to Relation 11, below.

FIG. 4A illustrates an exemplary plot 410 of dose-rate versus dose for a plurality of voxels 420 of an exemplary treatment plan, in accordance with embodiments of the present invention. As used herein, the term "voxel" is used to refer to and/or describe a unit of graphic information that defines a point or small volume in a three dimensional space. Plot 410 is one representation and/or display of a treatment plan. The voxels 420 generally correspond to a particular patient tissue of interest, although the voxels 420 may indicate other structures, in some embodiments. A first portion 424, indicated by open circles, of voxels 420 are below a dose rate minimum, DRmin 430. DRmin 430 may be user selectable, in some embodiments. A second portion, 426, indicated by closed circles, of voxels 420 are above the dose rate minimum, DRmin 430. The dose rate minimum is a dose rate of interest to a clinician and is not required to be a fixed value. The dose rate minimum may correspond to a FLASH radiotherapy dose rate, in accordance with embodiments of the present invention.

In accordance with embodiments of the present invention, a novel "FLASH Index" may be generated as a ratio of the number of voxels above a dose rate minimum, e.g., above dose rate minimum, DRmin 430, divided by the total number of voxels. This FLASH Index ratio expresses a ratio, e.g., a percentage, of voxels 420 that are above the selected dose rate minimum. If the dose rate minimum corresponds to a FLASH radiotherapy threshold, e.g., 40 Gy/s, this ratio indicates a ratio or percentage of a treatment plan that beneficially has FLASH characteristics. Relation 440 of FIG. 4A illustrates determination of a FLASH Index, corresponding to the graphical plot 410, in accordance with embodiments of the present invention.

Relation 6, below, may be used to determine a FLASH Index, in accordance with embodiments of the present invention.

FLASH Index=number 426/total number(426+424) (Relation 6)

FIG. 4B illustrates an exemplary plot 450 of dose-rate versus dose for a plurality of voxels 455 of an exemplary treatment plan, in accordance with embodiments of the present invention. Plot 450 is one representation and/or display of a treatment plan. The voxels 455 generally correspond to a particular patient tissue of interest, although the voxels 455 may indicate other structures, in some embodiments. In addition to indicating a dose rate minimum, DRmin 431, similar to dose rate minimum, DRmin 430 of FIG. 4A, plot 450 also indicates a dose minimum, Dmin 457.

The two segmentation lines DRmin 431 and Dmin 457, divide the voxels 455 into four quadrants. The voxels 455 are segmented into voxels 460 that are above the dose rate minimum, DRmin 431, and above the dose minimum, Dmin 457. DRmin 431 and/or Dmin 457 may be user selectable, in some embodiments. The remaining voxels 470 are below the dose rate minimum, DRmin 431 and/or below the dose minimum, Dmin 457.

In accordance with embodiments of the present invention, a novel "FLASH Index" may be generated as a ratio of the number of voxels above both the dose rate minimum, DRmin 431 and above the dose minimum, Dmin 457, divided by the total number of voxels. This FLASH Index ratio expresses a ratio, e.g., a percentage, of voxels 455 that are above the selected dose rate minimum and above the dose minimum. If the dose rate minimum corresponds to a FLASH radiotherapy threshold, e.g., 40 Gy/s, and the dose minimum, e.g., 10 Gy, this ratio indicates a ratio or percentage of a treatment plan that beneficially has FLASH characteristics. The minimum dose value is exemplary, and represents a dose at which a FLASH effect might be observed, independent of a prescribed dose Relation 480 of FIG. 4B illustrates determination of a FLASH Index, corresponding to the graphical plot 450, in accordance with embodiments of the present invention.

Relation 7, below, may be used to determine a FLASH Index, in accordance with embodiments of the present invention.

FLASH Index=number 460/total number(460+470) (Relation 7)

Figures 5A, 5B:
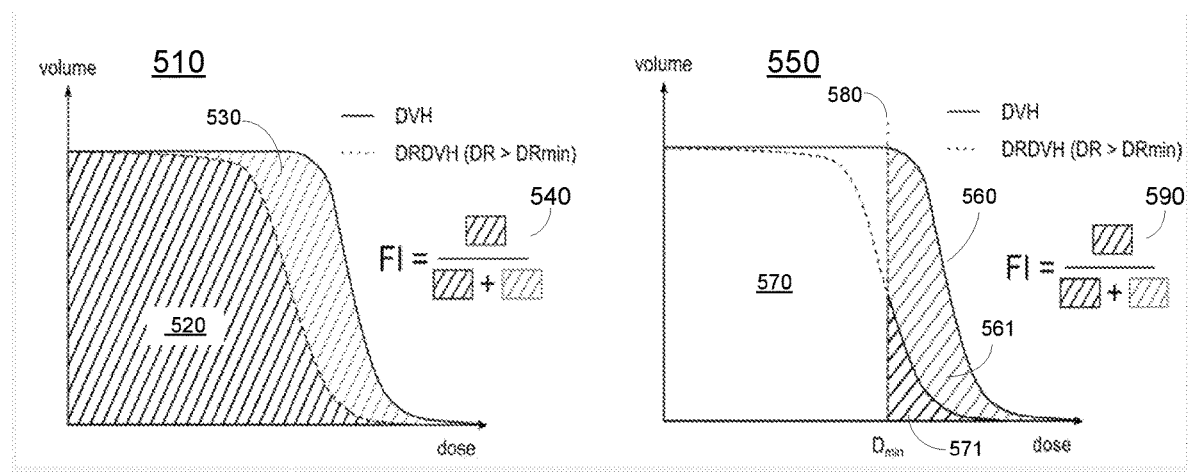
FIG. 5A illustrates an exemplary plot of dose versus volume for an exemplary treatment plan, in accordance with embodiments of the present invention.
FIG. 5B illustrates a second exemplary plot of dose versus volume for an exemplary treatment plan, in accordance with embodiments of the present invention.

FIG. 5A illustrates an exemplary plot 510 of dose versus volume for an exemplary treatment plan, in accordance with embodiments of the present invention. Plot 510 is one representation and/or display of a treatment plan. Plot 510 comprises a dose-volume histogram (DVH) 530 and a dose-rate dose-volume histogram (DRDVH) 520 overlaid on DVH 530. DRDVH 520 is plotted for dose rates above a minimum dose rate, DRmin.

In accordance with embodiments of the present invention, a novel "FLASH Index" may be generated as a ratio of the area of DRDVH 520 to the area of DVH 530. If the dose rate minimum corresponds to a FLASH radiotherapy threshold, e.g., 40 Gy/s, this ratio indicates a ratio or percentage of a treatment plan that beneficially has FLASH characteristics. The dose rate minimum may be user selectable, in some embodiments. Relation 540 of FIG. 5A illustrates determination of a FLASH Index, corresponding to the graphical plot 510, in accordance with embodiments of the present invention.

Relation 8, below, may be used to determine a FLASH Index, in accordance with embodiments of the present invention.

FLASH Index=area 520/total area(520+530)  (Relation 8)

FIG. 5B illustrates an exemplary plot 550 of dose versus volume for an exemplary treatment plan, in accordance with embodiments of the present invention. Plot 550 is one representation and/or display of a treatment plan. Plot 550 comprises a dose-volume histogram (DVH) 560 and a dose-rate dose-volume histogram (DRDVH) 570 overlaid on DVH 560. DRDVH 570 is plotted for dose rates above a minimum dose rate, DRmin. Plot 550 also indicates a minimum dose, Dmin 580. DRmin and/or Dmin 580 may be user selectable, in some embodiments.

In accordance with embodiments of the present invention, a novel "FLASH Index" may be generated as a ratio of the area 571 of DRDVH 570 above Dmin 580 to the area 561 of DVH 560 above Dmin 580. If the dose rate minimum corresponds to a FLASH radiotherapy threshold, e.g., 40 Gy/s, and the dose minimum, e.g., 10 Gy, this ratio indicates a ratio or percentage of a treatment plan that beneficially has FLASH characteristics. The minimum dose value is exemplary, and represents a dose at which a FLASH effect might be observed, independent of a prescribed dose Relation 590 of FIG. 5B illustrates determination of a FLASH Index, corresponding to the graphical plot 550, in accordance with embodiments of the present invention.

Relation 9, below, may be used to determine a FLASH Index, in accordance with embodiments of the present invention.

FLASH Index=area 571/total area(571+561)  (Relation 9)

A FLASH Plan Index, sometimes known as or referred to as a "Patient FLASH Index," may be determined for an overall treatment plan, e.g., encompassing all tissues and/or structures considered in a radiotherapy treatment plan. A FLASH Plan Index may be expressed as a combination of individual FLASH Indexes for each of the tissues and/or structures. Relation 10, below, may be used to determine a FLASH Plan Index based on averaging the individual FLASH Indexes, in accordance with embodiments of the present invention.

$$FI_{plan} = \frac{\sum_{OAR} FI_{OAR}}{N_{OAR}},$$  (Relation 10)

where $N_{OAR}$ is the number of individual FLASH Indexes.

Relation 11, below, may be used to determine a FLASH Plan Index based on a weighted average of the individual FLASH Indexes, in accordance with embodiments of the present invention.

$$FI_{plan} = \frac{\sum_{OAR} \alpha_{OAR} \cdot FI_{OAR}}{N_{OAR}},$$  (Relation 11)

where $\alpha_{OAR}$ is a ponderation factor accounting for the relative contribution of each structure. The $\alpha_{OAR}$ term may take into account the relative importance of sparing the organ, radio-sensitivity of an OAR, and/or the dose delivered to an organ, in accordance with embodiments of the present invention. For example, an OAR that receives a small radiation dose may receive a small weighting such that its FLASH Index does not greatly affect a FLASH Plan Index.

Figure 6:
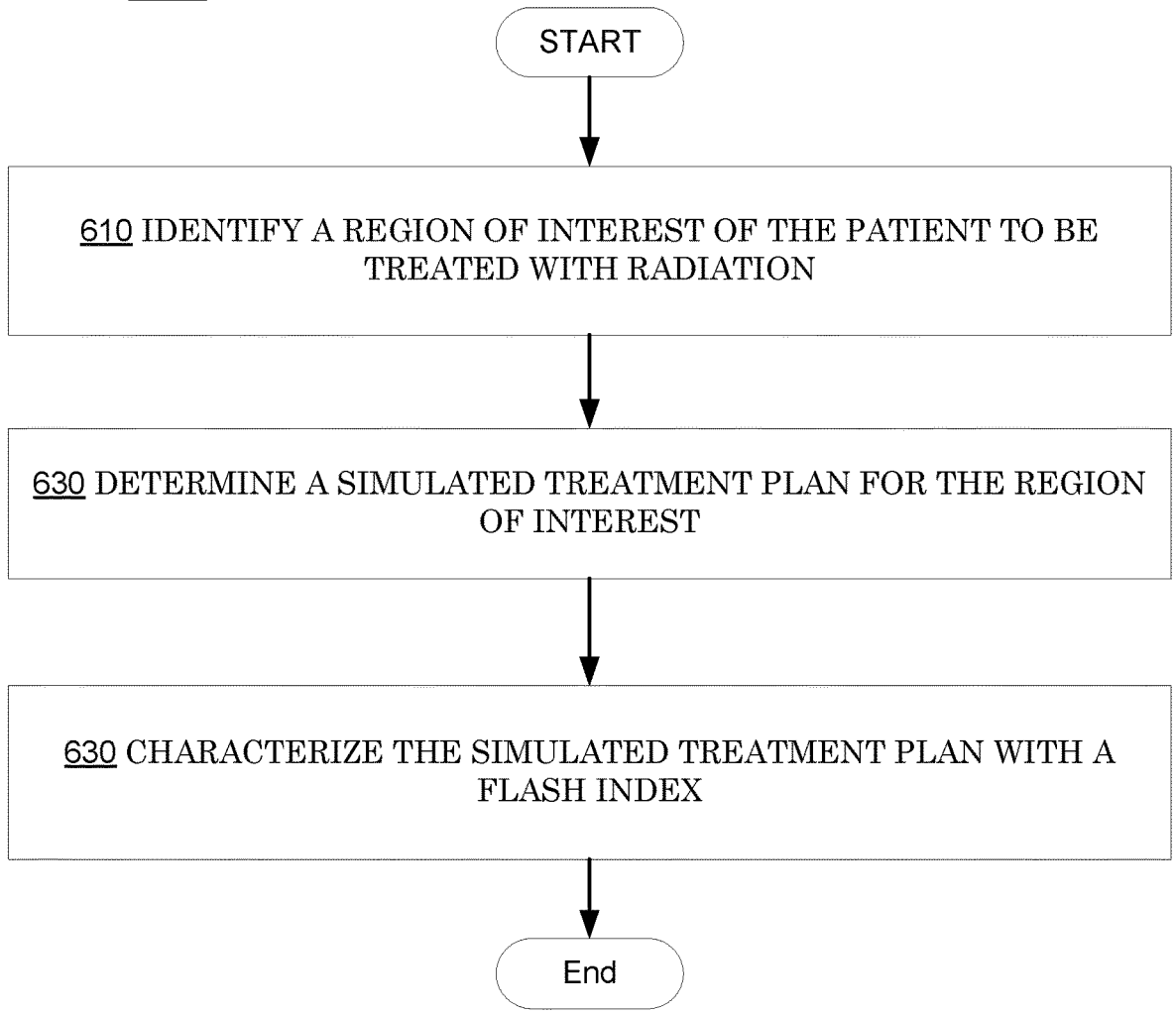
FIG. 6 illustrates an exemplary method of planning radiation treatment for a patient, in accordance with embodiments of the present invention.

FIG. 6 illustrates an exemplary method 600 of planning radiation treatment for a patient, in accordance with embodiments of the present invention. In 610, a region of interest of the patient is identified to be treated with radiation. The region may be a tumor, for example.

In 620, a simulated treatment plan for the region of interest is determined based on a statistical analysis between one or more metrics of the identified region of interest and a previously determined predictive dynamics database that includes information regarding the one or more metrics for corresponding regions of interest for a population of patients. The treatment plan may utilize planning system 200 (FIG. 2), for example.

In 630, the simulated treatment plan is characterized with a FLASH Index that compares an ideal FLASH radiation treatment plan to the simulated treatment plan.

Figure 7:
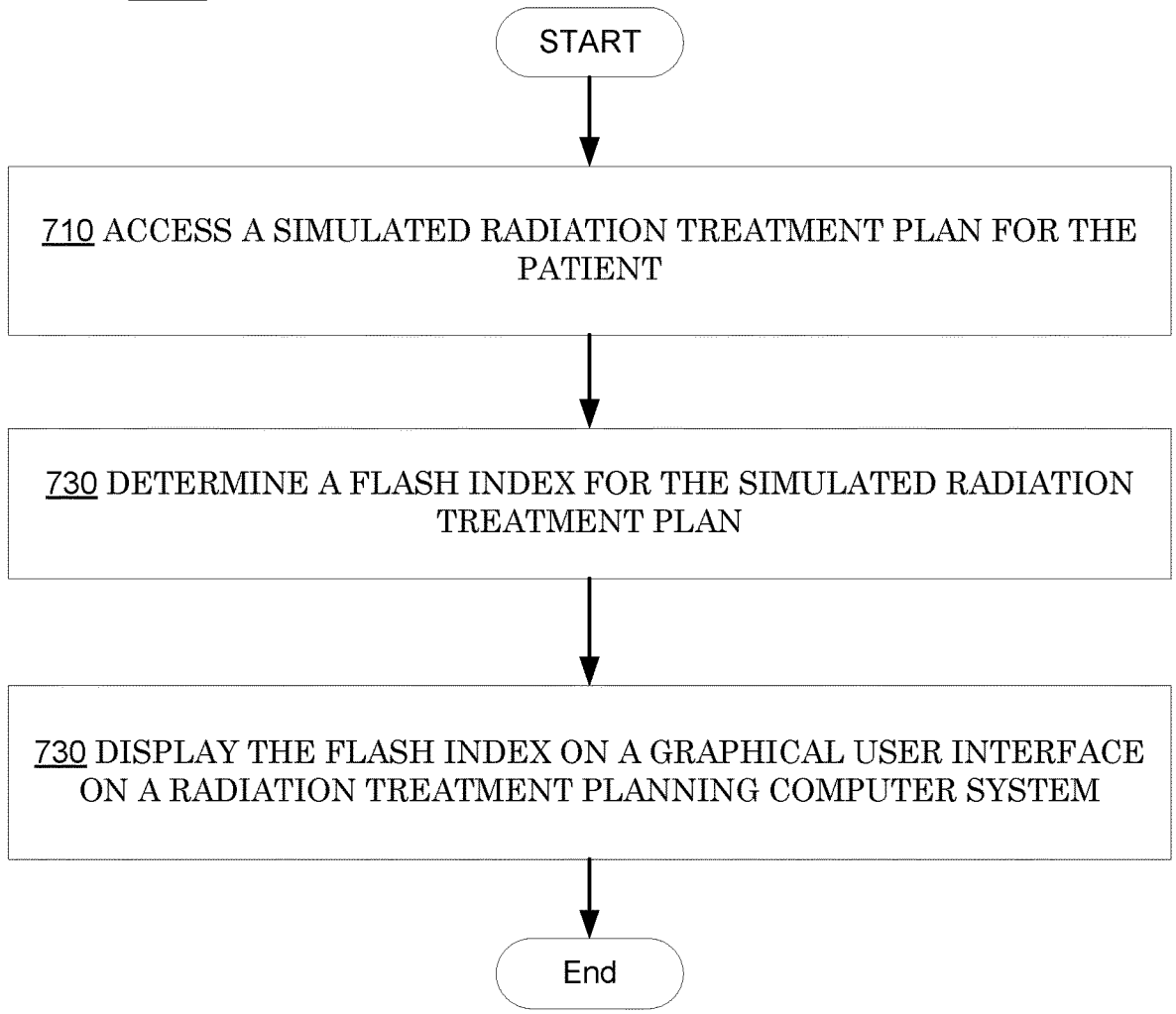
FIG. 7 illustrates another exemplary method of planning radiation treatment for a patient, in accordance with embodiments of the present invention.

FIG. 7 illustrates an exemplary method 700 of planning radiation treatment for a patient, in accordance with embodiments of the present invention. In 710, the method accesses a simulated radiation treatment plan for the patient. In 720, the method determines a FLASH Index for the simulated radiation treatment plan. In 730, the method displays the FLASH Index on a graphical user interface of a radiation treatment planning computer system. The FLASH Index may be for a specific region, tissue type, and/or organ at risk, in some embodiments. The display may also include a patient or FLASH Plan Index, in some embodiments. Exemplary displays of a FLASH Index are presented in FIGS. 8A and 8B, below.

Figure 8A:
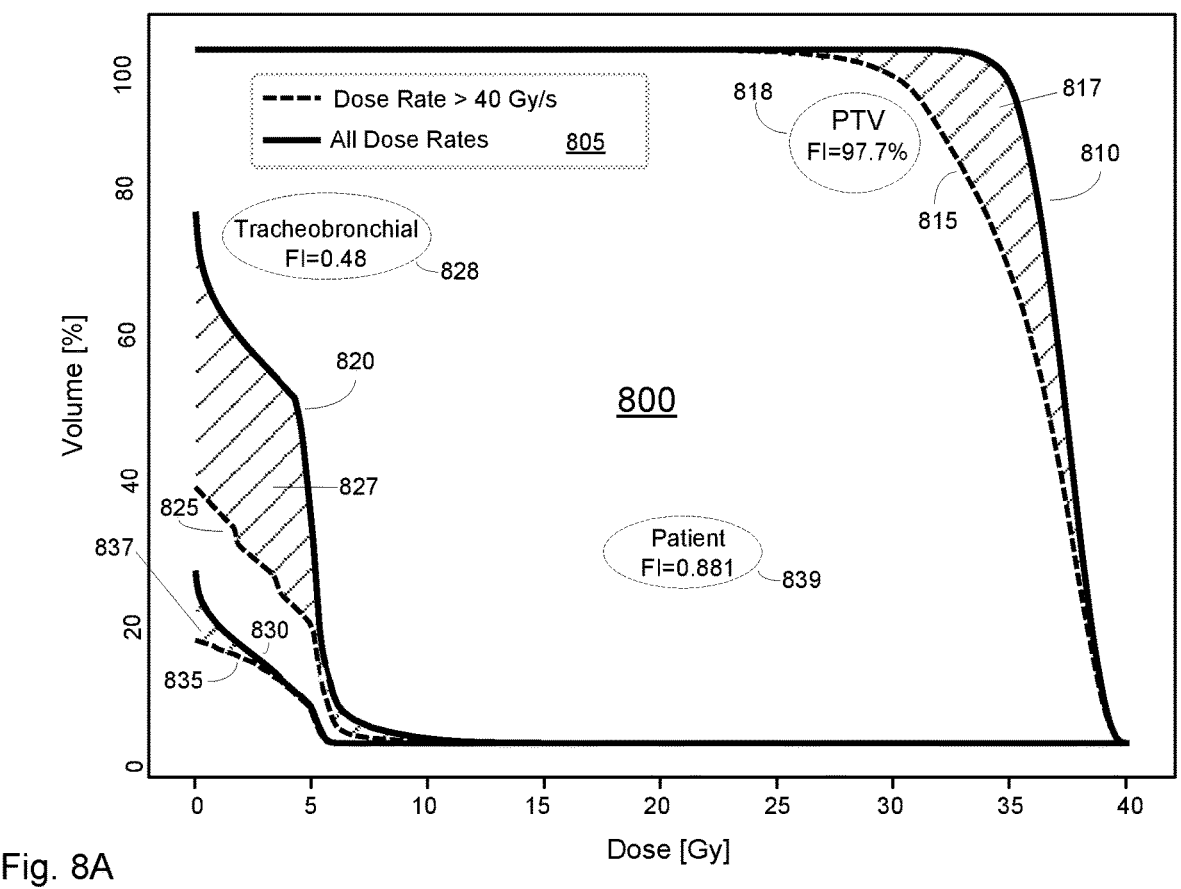
FIG. 8A illustrates an exemplary display image of a Dose-Volume Histogram (DVH) determined for a simulated treatment plan, in accordance with embodiments of the present invention.

FIG. 8A illustrates an exemplary display image 800 of a Dose-Volume Histogram (DVH) determined for a simulated treatment plan, in accordance with embodiments of the present invention. Image 800 may be displayed on or by display device 225 (FIG. 2). In display image 800, solid curves represent a DVH for one type of tissue and/or organ, and a dashed curve represents a DRDVH for one type of tissue and/or organ. Legend 805 may display legend information for such display elements.

In the example of FIG. 8A, each set of curves represents a single tissue type and/or organ at risk (OAR). Solid line curve 810 represents all radiotherapy dose rates that are simulated to be delivered to a planning target volume (PTV), for example, a lung tumor. In accordance with embodiments of the present invention, dashed line curve 815 represents radiotherapy dose rates that are above, for example, 40 Gy/s for the PTV. The threshold for generating curve 815 may be changed, in some embodiments. Area 817 provides a visual indication of a difference between curve 810 and novel curve 815. Area 817 may be visually identified by graphical elements, for example, area 817 may be cross-hatched. As previously presented, a FLASH Index for the PTV may be determined based on differences between a total radiotherapy dose rate, e.g., as represented by solid line curve 810, and radiotherapy dose rates that are above 40 Gy/s, e.g., as represented by dashed line curve 815. Optional alphanumeric notation 818 may identify the curve set (810, 815), e.g., as "PTV." Optional alphanumeric notation 818 may also display a FLASH Index for the PTV, e.g., 97.7%. In accordance with embodiments of the present invention, a FLASH Index may be expressed and/or displayed as a ratio, for example, a number between 0 and 1, and/or as a percentage.

In a similar manner, solid line curve 820 represents all radiotherapy dose rates that are simulated to be delivered to a tracheobronchial region. In accordance with embodiments of the present invention, dashed line curve 825 represents radiotherapy dose rates that are above, for example, 40 Gy/s for the tracheobronchial region. Area 827 provides a visual indication of a difference between curve 820 and novel curve 825. Area 827 may be visually identified by graphical elements, for example, area 827 may be cross-hatched. A FLASH Index for the tracheobronchial region may be determined based on differences between a total radiotherapy dose rate, e.g., as represented by solid line curve 820, and radiotherapy dose rates that are above 40 Gy/s, e.g., as represented by dashed line curve 825. Optional alphanumeric notation 828 may identify the curve set (820, 825), e.g., as "Tracheobronchial." Optional alphanumeric notation 828 may also display a FLASH Index for the tracheobronchial region, e.g., 0.48.

Solid line curve 830 represents all radiotherapy dose rates that are simulated to be delivered to an esophageal region. In accordance with embodiments of the present invention, dashed line curve 835 represents radiotherapy dose rates that are above, for example, 40 Gy/s for the esophageal region. Area 837 provides a visual indication of a difference between curve 830 and novel curve 835. Area 837 may be visually identified by graphical elements, for example, area 837 may be cross-hatched. A FLASH Index for the esophageal region may be determined based on differences between a total radiotherapy dose rate, e.g., as represented by solid line curve 830, and radiotherapy dose rates that are above 40 Gy/s, e.g., as represented by dashed line curve 835. An optional alphanumeric notation (not shown) may provide similar identification and/or information for the esophageal region curve set (830, 835).

In accordance with embodiments of the present invention, any number of treatment regions, tissues, and/or organs at risk (OARs) may be displayed within image 800. In addition to the exemplary PTV (810, 815, 817) tracheobronchial region (820, 825, 827), and/or esophageal region (830, 835, 837) curves and areas illustrated in FIG. 8A, myriad other curves and areas for other treatment regions, tissues, and/or organs at risk (OARs) may be displayed in any combination. Displayed treatment regions, tissues, and/or organs at risk (OARs), may include, for example, PTV, Spinal Cord, Heart, Esophagus, Tracheobronchial, Lungs-gross tumor volume (GTV), and/or Great Vessels. Other treatment regions, tissues, and/or OARs may be included as well. An overall patient treatment plan, for example comprising a FLASH Plan Index, may also be displayed, for example as alphanumeric notation 839. Each displayed set of curves and areas may include an associated alphanumeric notation similar to alphanumeric notation 818, in embodiments.

In accordance with embodiments of the present invention, each curve set, e.g., PTV curve set 810, 815, area, e.g., 817, and/or alphanumeric notation, e.g., notation 818, may be displayed in a unique color to provide visual identification and differentiation among the multiple treatment regions, tissues, and/or organs at risk (OARs) that may be displayed. For example, PTV curve set 810, 815, area, e.g., 817, and/or alphanumeric notation 818, may be displayed in an "aqua" color. Tracheobronchial region curve set 820, 825, area, e.g., 827, and/or alphanumeric notation 828 may be displayed in a "yellow" color. Esophageal region curve set 830, 835, area, e.g., 837, and/or an Esophageal region alphanumeric notation (not shown) may be displayed in a "red" color. A Spinal Cord curve set, area, and/or alphanumeric notation (not shown) may be displayed in a "green" color. A Heart curve set, area, and/or alphanumeric notation (not shown) may be displayed in a "pink" color. A Lungs-GTV curve set, area, and/or alphanumeric notation (not shown) may be displayed in a "blue" color. A Great Vessels curve set, area, and/or alphanumeric notation (not shown) may be displayed in a "violet" color. A Patient curve set, area (not shown), and/or alphanumeric notation, e.g., alphanumeric notation 839, may be displayed in a "tan" color. All such color associations are exemplary.

In accordance with embodiments of the present invention, display color(s) associated with treatment regions, tissues, and/or organs at risk (OARs) may be selected by a user, or may be automatically selected by a treatment planning system. In some embodiments, some display elements, e.g., curves 810, 815, area 817, and/or alphanumerics 818, may be selected, either manually or automatically, to visually highlight a specific treatment region, tissue type, and/or organ at risk (OAR) of particular interest or concern in a radiotherapy treatment planning process. Visual highlights may comprise, for example, colors, brightness, and/or increased intensity, in some embodiments. Alphanumeric elements, e.g., alphanumeric notation 818, may be presented in a different, larger, and/or bold typeface, for example.

FIG. 8B illustrates an exemplary display image 850 of a Display Legend for documenting and explaining display image 800 of FIG. 8A, in accordance with embodiments of the present invention. Display Image 850 may be displayed in association with display image 800, e.g., above, below, or to a side of display image 800, in some embodiments.

Display Image 850 displays a solid line 852 to identify that solid line curve 810 (FIG. 8A) represents all dose rates for a PTV. Display Image 850 also displays dashed line 854 to identify that dashed line curve 815 represents radiotherapy dose rates that are above, for example, 40 Gy/s for the PTV. Display Image 850 may also comprise alphanumeric legend information, including, for example, a dose rate ("DR") criteria display 856 that identifies a dose rate used to determine a dashed line curve, e.g., dashed line curve 815 (FIG. 8A). In the embodiment of FIG. 8B, dose rate criteria display 856 indicates that dashed line curve 815 represents radiotherapy dose rates that are greater than 40 Gy/s, for the PTV. Display image 850 may also comprise a display 858 of a Flash Index corresponding to a particular treatment region, tissue, and/or OAR.

Display Image 850 may comprise similar display elements for a variety of treatment regions, tissues, and/or OARs. As illustrated, display image 850 includes legend information, dose rate criteria 856, and a FLASH Index 858 for PTV, Spinal Cord 860, Heart 865, Esophagus 870, Tracheobronchial region 875, Lungs-GTV 880, and Great Vessels 885. Display image 850 also includes legend information, dose rate criteria and a FLASH Index, or FLASH Plan Index, 890 for the patient. As previously presented, a FLASH Index may be expressed and/or displayed as a ratio, for example, a number between 0 and 1, and/or as a percentage. Display Image 850 shows examples of FLASH Indexes presented as ratios and as percentages.

In accordance with embodiments of the present invention, solid line 852, dashed line 854, and/or associated legend alphanumerics, e.g., display images 856 and/or 858, may be displayed in the same color(s) as corresponding elements of display image 800 (FIG. 8A). For example, solid line 852, dashed line 854, display images 856 and/or 858 may be displayed in the same color as PTV curve set 810, 815, area, e.g., 817, and/or alphanumeric notation, e.g., notation 818, of display image 800 (FIG. 8A). For example, consistent with the exemplary color scheme previously presented with respect to display image 800, information related to a display of PTV information including solid line 852, dashed line 854, dose rate ("DR") criteria display 856, and/or Flash Index 858 may be displayed in an "aqua" color.

In accordance with embodiments of the present invention, one or both of display image 800 (FIG. 8A) and/or display image 850 (FIG. 8B) may be displayed. Display image 850 may present information for greater or fewer treatment regions, tissues, and/or OARs in comparison to those elements displayed in image 800. For example, image 850 may present information, including, for example, a dose rate criteria and/or a FLASH Index for a heart while information of the heart is not displayed in image 800.

Embodiments in accordance with the present invention provide systems and methods systems and methods for characterizing a FLASH radiotherapy plan. In addition, embodiments in accordance with the present invention provide systems and methods that compare an ideal FLASH radiation treatment plan to a simulated treatment plan. Further, embodiments in accordance with the present invention provide systems and methods that compare an ideal FLASH radiation treatment plan to a simulated treatment plan for a plurality of organs at risk. Still further, embodiments in accordance with the present invention provide systems and methods for characterizing a FLASH radiotherapy plan that are compatible and complementary with existing systems and methods of planning and/or administering radiotherapy.

Although the invention has been shown and described with respect to a certain exemplary embodiment or embodiments, equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

Various embodiments of the invention are thus described. While the present invention has been described in particular embodiments, it should be appreciated that the invention should not be construed as limited by such embodiments, but rather construed according to the below claims.

We claim:

1. A method of planning radiation treatment for a patient, the method comprising:
    identifying a region of interest of said patient to be treated with radiation;
    determining a simulated treatment plan for said region of interest based on a statistical analysis between one or more metrics of said identified region of interest and a previously determined predictive dynamics database that includes information regarding said one or more metrics for corresponding regions of interest for a population of patients; and
    characterizing said simulated treatment plan with a FLASH Index that compares an ideal FLASH radiation treatment plan to said simulated treatment plan, wherein
        the FLASH index includes a FLASH Plan Index encompassing all organs at risk, and
        the FLASH Plan Index includes an average of a plurality of FLASH Indexes, each of the FLASH Indexes corresponding to a single organ at risk.

2. The method of claim 1, wherein said FLASH Index is for a single organ at risk.

3. The method of claim 1, wherein the average of the plurality of FLASH Indexes is a weighted average of the plurality of FLASH Indexes.

4. The method of claim 3, wherein a weight of a FLASH Index for a single organ at risk corresponds to a radio sensitivity of the single organ at risk.

5. The method of claim 1, wherein said FLASH Index comprises a result of a function divided by a total number of voxels contained in the region of interest, the function being a sum of Heaviside function values of dose rate for each voxel minus a minimum dose rate.

6. The method of claim 1, wherein said FLASH Index comprises a result of a function divided by a total number of voxels contained in the region of interest, the function being a sum of Heaviside function values of dose rate for each voxel minus a minimum dose rate multiplied by a Heaviside function value of dose for each voxel minus a minimum dose.

7. The method of claim 1, wherein said FLASH Index comprises a result of a function divided by a total number of voxels contained in the region of interest, the function being a sum of Heaviside function values of dose rate for each voxel minus a minimum dose rate multiplied by a Heaviside function value of dose for each voxel minus a minimum dose multiplied by a Heaviside function of irradiation time for each voxel minus a maximum irradiation time.

8. The method of claim 1, wherein said FLASH Index comprises a result of a function divided by a total number of voxels contained in the region of interest, the function being a sum of Heaviside function values of dose rate for each voxel minus a minimum dose rate multiplied by a quantity one minus an exponential function of negative alpha multiplied by a radiation dose for each voxel.

9. A method of planning radiation treatment for a patient, the method comprising:
    accessing a simulated radiation treatment plan for the patient;
    determining a FLASH Index for the simulated radiation treatment plan; and
    displaying the FLASH Index on a graphical user interface on a radiation treatment planning computer system, wherein
        the FLASH index includes a FLASH Plan Index encompassing all organs at risk, and
        the FLASH Plan Index includes an average of a plurality of FLASH Indexes, each of the FLASH Indexes corresponding to a single organ at risk.

10. The method of claim 9, wherein the FLASH Index corresponds to a single organ at risk.

11. The method of claim 9, wherein the FLASH Index corresponds to a plurality of organs at risk.

12. The method of claim 9, wherein the FLASH Index is expressed as a ratio between zero and one.

13. A non-transitory computer-readable storage medium having computer-executable instructions for causing a computer system to perform a method used for planning radiation treatment, the method comprising:
    identifying a region of interest of a patient to be treated with radiation;

determining a simulated treatment plan for said region of interest based on a statistical analysis between one or more metrics of said identified region of interest and a previously determined predictive dynamics database that includes information regarding said one or more metrics for corresponding regions of interest for a population of patients;

characterizing said simulated treatment plan with a FLASH Index that compares an ideal FLASH radiation treatment plan to said simulated treatment plan; and displaying said FLASH Index on a graphical user interface of said computer system, wherein the FLASH index includes a FLASH Plan Index encompassing all organs at risk, and the FLASH Plan Index includes an average of a plurality of FLASH Indexes, each of the FLASH Indexes corresponding to a single organ at risk.

14. The non-transitory computer-readable storage medium of claim 13, wherein said FLASH Index is for a single organ at risk.

15. The non-transitory computer-readable storage medium of claim 13, wherein the FLASH Plan Index encompasses a plurality of organs at risk.

16. The non-transitory computer-readable storage medium of claim 13, wherein said FLASH Index comprises a comparison of a number of voxels above a dose rate minimum to a total number of voxels of the simulated treatment plan.

17. The non-transitory computer-readable storage medium of claim 13, wherein said FLASH Index comprises a ratio of a number of voxels that are above a selected dose rate minimum and above a dose minimum divided by a total number of voxels of the simulated treatment plan.

18. The non-transitory computer-readable storage medium of claim 13, wherein said FLASH Index comprises a comparison of a dose-volume histogram to a dose-rate dose-volume histogram for the simulated treatment plan.

19. The non-transitory computer-readable storage medium of claim 13, wherein the FLASH Index is displayed as a percentage.

* * * * *